US011712223B2

(12) United States Patent
Wissel et al.

(10) Patent No.: US 11,712,223 B2
(45) Date of Patent: Aug. 1, 2023

(54) ULTRASOUND IMAGING SYSTEM AND METHOD

(71) Applicant: KONINKLIJKE PHILIPS N.V., Eindhoven (NL)

(72) Inventors: Tobias Wissel, Lübeck (DE); Frank Michael Weber, Hamburg (DE); Jochen Peters, Norderstedt (DE); Arne Ewald, Hamburg (DE); Alexander Schmidt-Richberg, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 127 days.

(21) Appl. No.: 17/045,303

(22) PCT Filed: Mar. 28, 2019

(86) PCT No.: PCT/EP2019/057853
§ 371 (c)(1),
(2) Date: Oct. 5, 2020

(87) PCT Pub. No.: WO2019/192921
PCT Pub. Date: Oct. 10, 2019

(65) Prior Publication Data
US 2021/0145410 A1    May 20, 2021

(30) Foreign Application Priority Data

Apr. 5, 2018    (EP) .................................... 18165863

(51) Int. Cl.
*A61B 8/08*    (2006.01)
*A61B 8/00*    (2006.01)
(Continued)

(52) U.S. Cl.
CPC .............. *A61B 8/5207* (2013.01); *A61B 8/02* (2013.01); *A61B 8/5223* (2013.01); *A61B 8/54* (2013.01);
(Continued)

(58) Field of Classification Search
CPC ....... A61B 8/5207; A61B 8/02; A61B 8/5223; A61B 8/54; A61B 8/5269; G01S 7/52026; G01S 15/8906
See application file for complete search history.

(56) References Cited

U.S. PATENT DOCUMENTS

2005/0251013 A1    11/2005    Krishnan et al.
2008/0009733 A1*    1/2008    Saksena ................. A61B 5/411
                                                          600/443

(Continued)

FOREIGN PATENT DOCUMENTS

EP    2807978 A1    12/2014
JP    2011005312 A    1/2011
(Continued)

OTHER PUBLICATIONS

International Search and Written Opinion for International Application No. PCT/EP2019/057853, filed Mar. 28, 2019, 12 pages.
(Continued)

*Primary Examiner* — Joseph M Santos Rodriguez
*Assistant Examiner* — Kaitlyn E Sebastian (57) ABSTRACT

An ultrasound imaging system for acquiring ultrasound images of an anatomical feature of interest in a subject, comprising a controller operable by a user and configured to: process input ultrasound images to extract anatomical data; determine a set of constraints to be applied to the ultrasound images, the constraints being spatial, temporal and/or of image quality, derived from the extracted anatomical data and/or on user input; monitor the ultrasound images, as they are received, for determining their compliance with the determined constraints; and output an indication based on the determined compliance. The user can adapt the imaging process using the feedback of these indications, and can decide to stop the process based on satisfactory indications.

20 Claims, 6 Drawing Sheets

(51) Int. Cl.
G01S 7/52 (2006.01)
G01S 15/89 (2006.01)
A61B 8/02 (2006.01)

(52) U.S. Cl.
CPC ...... G01S 7/52026 (2013.01); G01S 15/8906 (2013.01)

(56) References Cited

U.S. PATENT DOCUMENTS

| | | | |
|---|---|---|---|
| 2013/0190600 A1* | 7/2013 | Gupta | A61B 8/0866 600/407 |
| 2016/0081663 A1 | 3/2016 | Chen et al. | |
| 2016/0143627 A1 | 5/2016 | Vignon et al. | |
| 2017/0273669 A1 | 9/2017 | Schneider | |
| 2019/0184204 A1* | 6/2019 | Ramamurthy | A61B 8/466 |
| 2019/0365348 A1* | 12/2019 | Toume | A61B 8/065 |

FOREIGN PATENT DOCUMENTS

| | | | | |
|---|---|---|---|---|
| WO | WO-2015191414 A2 * | 12/2015 | ........... | G06K 9/6249 |
| WO | 2016038491 A1 | 3/2016 | | |

OTHER PUBLICATIONS

Ecabert, et al., "Automatic Model-Based Segmentation of the Heart in CT Images Medical Imaging", IEEE Transactions on Medical Imaging, Sep. 2008, vol. 27, Issue 9, pp. 1189-1201 (Abstract).

Kasel, et al., "Standardized Imaging for Aortic Annular Sizing: Implications for Transcatheter Valve Selection", JACC Cardiovascular Imaging, Feb. 2013, vol. 6, Issue 2, pp. 249-262.

* cited by examiner

ULTRASOUND IMAGING SYSTEM AND METHOD

RELATED APPLICATIONS

This application is the U.S. National Phase application under 35 U.S.C. § 371 of International Application No. PCT/EP2019/057853, filed on Mar. 28, 2019, which claims the benefit of European Application No. 18165863.4, filed Apr. 5, 2018. These applications are hereby incorporated by reference herein.

FIELD OF THE INVENTION

This invention relates to an ultrasound imaging system and method. It is applicable to cardiovascular imaging for the diagnosis or treatment of cardiovascular disease, and to the imaging of other anatomical regions of interest in a subject.

BACKGROUND OF THE INVENTION

Ultrasound plays an essential role in cardiovascular imaging. In this context, diagnosis and treatment planning often rely upon a clear delineation of relevant anatomical sites such as the ventricles, the atria or surrounding vessels. A heart model is disclosed in WO 2016/142204 A1. The heart model may be used after imaging as an aid to subject the mapped cardiac structure in the ultrasound imagery to segmentation algorithms in order to obtain the dimensions of interest of the cardiac anatomical sites under investigation, e.g. by mapping such a model onto a volumetric image. This process has been automated for single frames or a time series of frames by using anatomically intelligent model-based segmentation, where generic, shape-constrained models are fitted to the imaging data [Ecabert, O.; Peters, J.; Schramm, H.; Lorenz, C.; von Berg, J.; Walker, M.; Vembar, M.; Olszewski, M.; Subramanyan, K.; Lavi, G. & Weese, J. Automatic Model-Based Segmentation of the Heart in CT Images Medical Imaging, IEEE Transactions on, 2008, 27, pp. 1189-1201]. This process similarly applies to the placement of models of other anatomical features of interest, e.g. organ models, foetal models and so on.

An accurate delineation, and consequently subsequent quantitative measurements for a specific clinical application, impose certain requirements on the image acquisition. Depending on the application, these can be temporal, spatial and/or image quality (such as image contrast) constraints. During live acquisition it is often very challenging for the sonographer to simultaneously take all constraints into account.

Spatially, for instance, a 3D image covers a certain field of view. As an example, in order to quantify the ejection fraction of the left ventricle (LV) in a transthoracic echocardiogram, TTE, the entire chamber is required in the field of view for at least both end systole and end diastole. By quickly adapting the model to the live acquisition (as a background process), the model notices that parts of the LV are outside the field of view. For illustration purposes, the 3D data then need to be mapped into a 2D space by projection or cutting planes, so that the sonographer always misses certain parts of the data or may struggle to quickly set all the visual information into context. This also entails a challenge to guarantee a certain image quality standard at all relevant image parts, whereas some of those parts may even be difficult to identify in the image in the first place.

Temporally, certain anatomical behavior may be either too fast for the sonographer to judge the image data during live view, or it may be difficult to maintain a certain acquisition state over one or several cardiac cycles. As an example, to characterize mitral valve regurgitation in TEE, the state of the valve leaflets (closed or open) needs to be tracked, e.g. to measure the valve orifice area.

For these reasons retrospective data analysis after storing the frames may suffer from insufficiently met requirements or poor reproducibility. At this time, repeating the recording may already be either inefficient or onerous or even not possible any more. The invention targets this problem and aims at better guidance and compliance to a set of constraints and/or guidelines.

SUMMARY OF THE INVENTION

The invention is defined by the claims.

According to examples in accordance with an aspect of the invention, there is provided an ultrasound imaging system for acquiring ultrasound images of an anatomical feature of interest in a subject, comprising:
an input for receiving the ultrasound images;
a controller operable by a user and configured to:
process the ultrasound images to extract anatomical data;
determine a set of constraints to be applied to the ultrasound images, the constraints being spatial, temporal and/or of image quality, derived from the extracted anatomical data and/or on user input;
monitor the ultrasound images, as they are received, for determining their compliance with the determined constraints;
and generate an indication based on the determined compliance;
and an output for providing the indication to the user.

The invention can enable a user to ensure that the images are compliant with predetermined standards, whilst acquiring the images in real time, so as to avoid the risk that the acquired set of images is inadequate. This would avoid the need to repeat the imaging process at least in part, which may be impractical or onerous. The indication can be given to the user in real time, and there can be one indication for each relevant constraint, showing its live status. A cumulative indication can also be given, indicating how well the constraints have been complied with over a recent period, for example over a cardiac cycle. An indication can also be given as to how well the constraints have been complied with by the best of the images input over a historic period, such as since the imaging process began—this can help the user decide whether sufficient imaging has been performed already.

The controller preferably comprises a segmentation processor configured to segment the ultrasound images in accordance with a mapped model of the anatomical feature of interest. This can help identify parts of the anatomical feature of interest and it can be used to automatically determine the constraints that are to be used in the monitoring process. It can also be used to determine whether the images comply with the constraints.

The system preferably comprises a database of image constraints in relation to anatomical data, the controller being configured to obtain the set of constraints from the database. This enables the system to obtain an optimal set of constraints for a given type of anatomical image, and the choice can be dependent on parts of the anatomy that the system has recognized from the images.

Guidelines for constraints are published in a number of sources and will be known to those skilled the art, for example:

Zamorano et al, "EAE/ASE Recommendations for the Use of Echocardiography in New Transcatheter Interventions for Valvular Heart Disease", Journal of the American Society of Echocardiography, Volume 24, Number 9, September 2011, pages 937-965.

For example, annular diameter is typically measured in systole, in a parasternal long-axis view, zoomed on the LVOT, left ventricular outflow tract; or it may be clinic-specific, or chosen according to personal preferences.

The system may receive physiological data relating to the subject from at least one body sensor and determine the compliance of the received ultrasound images with the determined constraints based at least in part on the physiological data. These physiological data may comprise an ECG or EMG from one or more body sensors, for example. The ECG can then help identify the heartbeat phase of the images, so as to apply a temporal constraint to the images. Alternative or additional sensors are possible, such as accelerations sensors to monitor the extent of body motion, so as to determine prohibitive time intervals i.e. times when measurements would be unreliable due to the motion and so should not be used.

The controller may be configured to store the ultrasound images and to compare the currently received ultrasound images with stored ultrasound images to determine the consistency of their degrees of compliance with the determined constraints, and to provide an indication to the user based on the determined consistency. This can be done over one heartbeat i.e. one cardiac cycle. It can also be done over a longer period, such as the period since the imaging process began; in this case, the system may indicate the level of compliance with the constraints of the best image obtained.

The controller is preferably configured to store the determined compliance of the ultrasound images over successive periods, to determine whether a predetermined image type has been received, and to provide an indication to the user based on whether this image type has been received. The predetermined image type can for example be one that satisfies one or more of the compliance constraints, which may include a constraint as to whether a measurement is consistent with a predetermined measurement, so that the user will know that this requirement has already been met and the process can safely be stopped when all such requirements have been met.

The controller is preferably configured to provide separate visual and/or aural indications to the user based on the determined compliance with different respective constraints of the ultrasound images over successive periods. This makes it intuitive and easy for the user to determine how well the imaging process is progressing in real time, and to adapt quickly to compensate for any inadequacy, for example by repositioning the probe or adapting the field of view or other imaging parameters.

The system may comprise a monitor arranged to display to the user the received ultrasound images, and a light display configured to display to the user the indication(s) based on the determined compliance. The monitor can of course be one that is normally part of a conventional imaging system, as it does not have to be specially adapted for use with this invention. Having the light display visible at the same time as the monitor enables the user to control the process fully in real time. The light display can be integrated with the image displayed on the monitor.

The controller may be configured to evaluate predetermined measurements from the extracted anatomical data and to provide an output to the user based on that evaluation. This exploits the monitored measurements more directly, so that they are used for more than setting constraints or determining constraint compliance. For example, the system could output a measurement of aortic valve diameter. These measurements can be used for compliance and consistency checks. Pre-defined measures may also be computed based on all the information extracted including anatomical data (spatial) and external sensor information (physiological, temporal . . . ) etc.

The ultrasound data can be of the heart of the subject and the controller can be configured to monitor them for compliance with a spatial constraint and with a temporal constraint in relation to the cardiac cycle.

The constraints can comprise a spatial constraint on the field of view or the location or angle of imaging the anatomical feature of interest, a temporal constraint on the period of imaging the anatomical feature of interest and/or an image quality constraint. These are useful gauges of the adequacy of the acquired images.

From another aspect the invention can provide a computer-implemented ultrasound imaging method of acquiring images of an anatomical feature of interest in a subject, comprising:

receiving the ultrasound images;

processing the ultrasound images to extract anatomical data;

determining a set of constraints to be applied to the ultrasound images, the constraints being spatial, temporal and/or of image quality, based on the extracted anatomical data and/or on user input;

monitoring the ultrasound images, as they are received, for determining their compliance with the determined constraints;

and providing an indication based on the determined compliance.

This method can use a system embodying the invention as described above.

The ultrasound imaging method can comprise receiving the ultrasound images until a predetermined image type has been received, providing an indication to the user that this image type has been received, and then continuing the process by receiving ultrasound images of a different image type. This gives the user confidence when all necessary image types have been acquired that the process can safely be stopped. It helps ensure that images are obtained with sufficient quality that there is no need to repeat any scanning of the patient.

From another aspect the invention can provide a computer program product comprising a computer readable storage medium having computer readable program instructions embodied therewith for, when executed on the controller of an ultrasound imaging system described above, causing the controller to implement the method described above. Such a computer program product for example may be used to enhance existing ultrasound image processing apparatuses by installation of the computer readable program instructions thereon.

These and other aspects of the invention will be apparent from and elucidated with reference to the embodiment(s) described hereinafter.

BRIEF DESCRIPTION OF THE DRAWINGS

Examples of the invention will now be described in detail with reference to the accompanying drawings, in which.

DETAILED DESCRIPTION OF THE EMBODIMENTS

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an ultrasound imaging system for acquiring ultrasound images of an anatomical feature of interest in a subject, comprising:

an input for receiving the ultrasound images;

a controller operable by a user and configured to:

process the ultrasound images to extract anatomical data;

determine a set of constraints to be applied to the ultrasound images, the constraints being spatial, temporal and/or of image quality, derived from the extracted anatomical data and/or on user input;

monitor the ultrasound images, as they are received, for determining their compliance with the determined constraints;

and generate an indication based on the determined compliance; and an output for providing the indication to the user.

Figure 1:
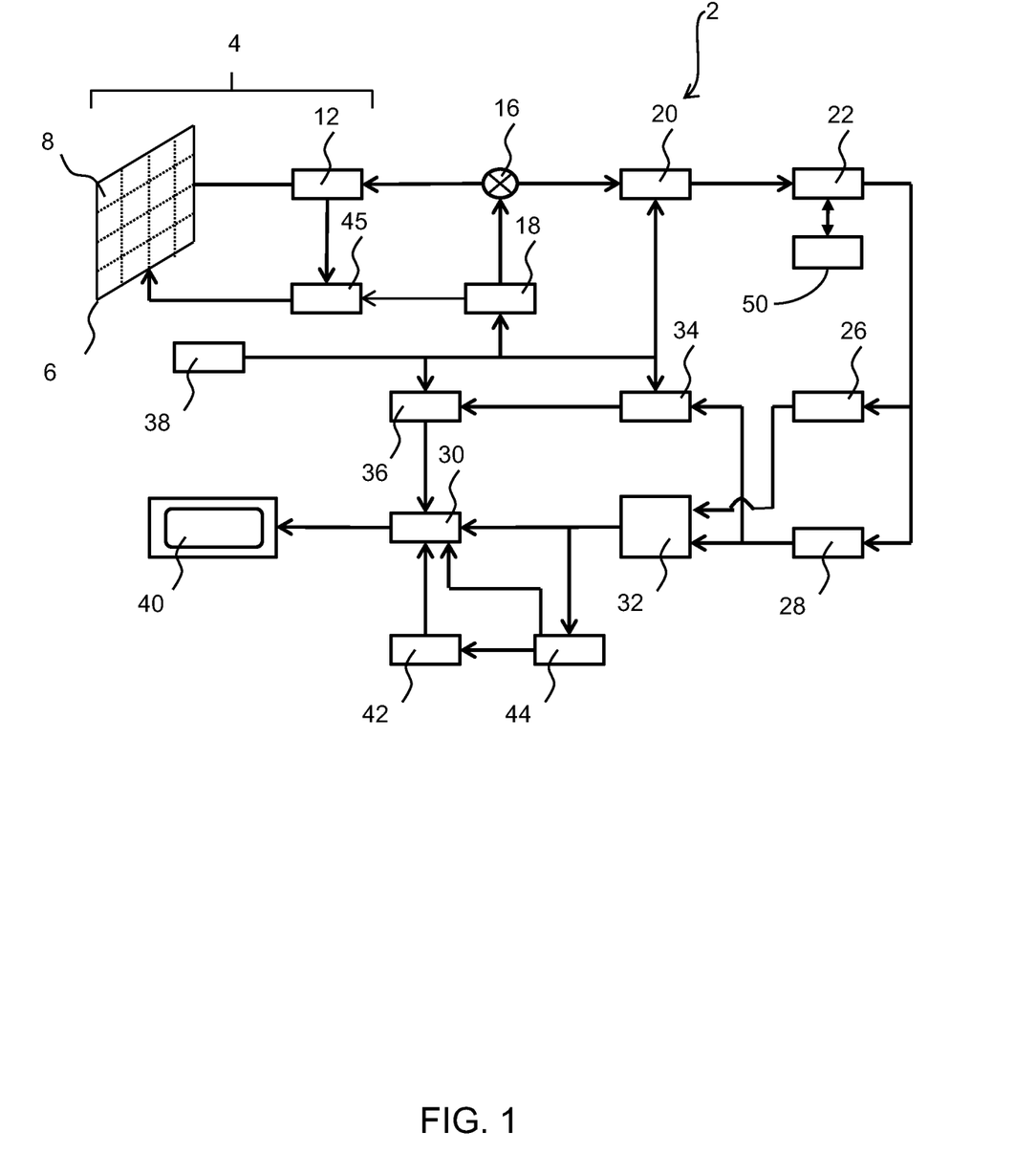
FIG. 1 shows an ultrasonic diagnostic imaging system.

FIG. 1 shows such an ultrasonic diagnostic imaging system 2 with an array transducer probe 4, in block diagram form.

The array transducer probe 4 comprises transducer cells. Traditionally, piezoelectric materials have been used for ultrasonic transducers. Examples are lead zirconate titanate (PZT) and polyvinylidene difluoride (PVDF) materials, with PZT being particularly popular as the material of choice. Single crystal piezoelectric materials are used to achieve high piezoelectric and electro-mechanical coupling constants for high performance transducers.

Recent developments have led to the prospect that medical ultrasound transducers can be batch manufactured by semiconductor processes. Desirably these processes should be the same ones used to produce the application specific integrated circuits (ASICs) needed by an ultrasound probe such as a CMOS process, particularly for 3D ultrasound. These developments have produced micro machined ultrasonic transducers or MUTs, the preferred form being the capacitive MUT (CMUT). CMUT transducers are tiny diaphragm-like devices with electrodes that convert the sound vibration of a received ultrasound signal into a modulated capacitance.

CMUT transducers in particular are able to function over a broad bandwidth, enable high resolution and high sensitivity imaging, and produce a large pressure output so that a large depth of field of acoustic signals can be received at ultrasonic frequencies.

FIG. 1 shows a transducer array 6 of CMUT cells 8 as discussed above for transmitting ultrasonic waves and receiving echo information. The transducer array 6 of the system 2 may generally be a one- or a two-dimensional array of transducer elements capable of scanning in a 2D plane or in three dimensions for 3D imaging.

The transducer array 6 is coupled to a micro-beamformer 12 which controls transmission and reception of signals by the CMUT array cells. Micro-beamformers are capable of at least partial beam forming of the signals received by groups or "patches" of transducer elements for instance as described in U.S. Pat. No. 5,997,479 (Savord et al.), U.S. Pat. No. 6,013,032 (Savord), and U.S. Pat. No. 6,623,432 (Powers et al.)

The micro-beamformer 12 is coupled by the probe cable, e.g. coaxial wire, to a transmit/receive (T/R) switch 16 which switches between transmission and reception modes and protects the main beam former 20 from high energy transmit signals when a micro-beamformer is not present or used and the transducer array 6 is operated directly by the main system beam former 20. The transmission of ultrasonic beams from the transducer array 6 under control of the micro-beamformer 12 is directed by a transducer controller 18 coupled to the micro-beamformer by the T/R switch 16 and the main system beam former 20, which receives input from the user's operation of the user interface or control panel 38. One of the functions controlled by the transducer controller 18 is the direction in which beams are steered and focused. Beams may be steered straight ahead from (orthogonal to) the transducer array 6, or at different angles for a wider field of view. The transducer controller 18 may be coupled to control a voltage source 45 for the transducer array. For instance, the voltage source 45 sets DC and AC bias voltage(s) that are applied to the CMUT cells of a CMUT array 6, e.g. to generate the ultrasonic RF pulses in transmission mode. The partially beam-formed signals produced by the micro-beamformer 12 are forwarded to the main beam former 20 where partially beam-formed signals from individual patches of transducer elements are combined into a fully beam-formed signal. For example, the main beam former 20 may have 128 channels, each of which receives a partially beam-formed signal from a patch of dozens or hundreds of CMUT transducer cells 8. In this way the signals received by thousands of transducer elements of a transducer array 6 can contribute efficiently to a single beam-formed signal.

The beam-formed signals are coupled to a signal processor 22. The signal processor 22 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles.

The signal processor 22 optionally may perform additional signal enhancement such as speckle reduction, signal compounding, and noise elimination. The bandpass filter in the signal processor 22 may be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals are coupled to a B-mode processor 26 and optionally to a Doppler processor 28. The B-mode processor 26 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 28, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B-mode (and Doppler) processor(s) are coupled to a scan converter 32 and a multiplanar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image.

The scan converter can overlay a B-mode structural image with colors corresponding to motion at points in the image field with their Doppler-estimated velocities to produce a color Doppler image which depicts the motion of tissue and blood flow in the image field. The multiplanar reformatter 44 will convert echoes which are received from points in a common plane in a volumetric region of the body into an ultrasonic image of that plane, for instance as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.)

The 2D or 3D images are coupled from the scan converter 32, multiplanar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B-mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name.

The user interface is also coupled to the transmit controller 18 to control the generation of ultrasound signals from the transducer array 6 and hence the images produced by the transducer array and the ultrasound system. The user interface is also coupled to the multiplanar reformatter 44 for selection and control of the planes of multiple multiplanar reformatted (MPR) images which may be used to perform quantified measures in the image field of the MPR images.

A controller 50 is connected to the signal processor 22, to provide the functionality of the present invention for determining compliance with predetermined constraints.

As will be understood by the skilled person, the above embodiment of an ultrasonic diagnostic imaging system is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the micro-beamformer 12 and/or the Doppler processor 28 may be omitted, the ultrasound probe 4 may not have 3D imaging capabilities and so on. The controller 50 may be part of the signal processor 22, and the functionality of both units 22 and 50 may be distributed in any arrangement of software and hardware. Other variations will be apparent to the skilled person. Generally, the invention may be embodied in an ultrasound workstation equipped with an ultrasound probe used to acquire the data.

The controller 50 of FIG. 1 will now be described with reference to FIG. 2.

The controller 50 is shown figuratively and has an input 52 for receiving ultrasound data from the signal processor 22, which it provides to an anatomical data extraction unit 54 comprising a model-based segmentation processor 56. An input unit 58 receives the ultrasound data and also anatomical data from the anatomical data extraction unit 54, as well as physiological data, such as ECG data, from a physiological sensor 60 on the patient's body. The input unit provides data to a constraints determination unit 62 which interacts with a constraints database 64 which may be part of the controller 50 or may be external and accessible by wired or wireless links (not shown). It will be apparent that the input to the system could alternatively take any of a variety of forms—an external (sensor) receiving unit can be provided to process the data into a format that makes it accessible for the determination of constraints.

A compliance monitoring unit 66 is arranged to receive determined constraints from the constraints determining unit 62 and the data from the input unit 58, to generate output data to a feedback unit 68 which communicates with a user interface 70. The user has an input unit 72 such as a keyboard and mouse or touchscreen, for providing user input to the user interface 70. This input unit 72 may of course be integrated with the user control panel 38. The user interface provides an output to a display 74, which may be the monitor 40 or a separate display, and which may also have an audible output such as a speaker, to indicate to the user the results of the processing by the controller 50.

During live acquisition, a real-time preview of the data is displayed on the monitor 40 to the user, who can trigger a recording. The system 2 has access to a database of stored recordings or at least a set of relevant measurements obtained from these stored recordings.

The compliance monitoring unit 66, in the back end of the application run by the controller 50, provides a set of constraints (spatial, temporal and/or image quality) and monitors compliance of the acquired ultrasound data with these constraints. This set may originate from a manual user input, through the user interface 70, or from the database 64, which stores pre-defined constraints taken from guideline documents related to specific applications or interventions.

The feedback unit 68 takes the monitoring result from the compliance monitoring unit 66 and provides an output, through the user interface 70 to the display 74, that illustrates the current status of the ultrasound imaging as well as compliance measures for the user. Compliance may either relate to how well the constraints have been met or to consistency with some user defined quantities relevant for the application (e.g. aortic valve diameter). The display may include traffic light-like indicators, to give the user a clear and intuitive indication of status for each of a number of constraints (spatial, temporal and/or image quality; current and historic/cumulative). Depending on the degree of conformity, a color ranging from green via yellow to red could be displayed. Using this visual feedback, the user can adjust his acquisition or ensure reproducibility of the measurements at the time of the patient examination, i.e. in real time. The display 74 may also include a speaker for providing an audible output to inform the user of the status of the imaging, to complement the visual indication.

Figure 3:
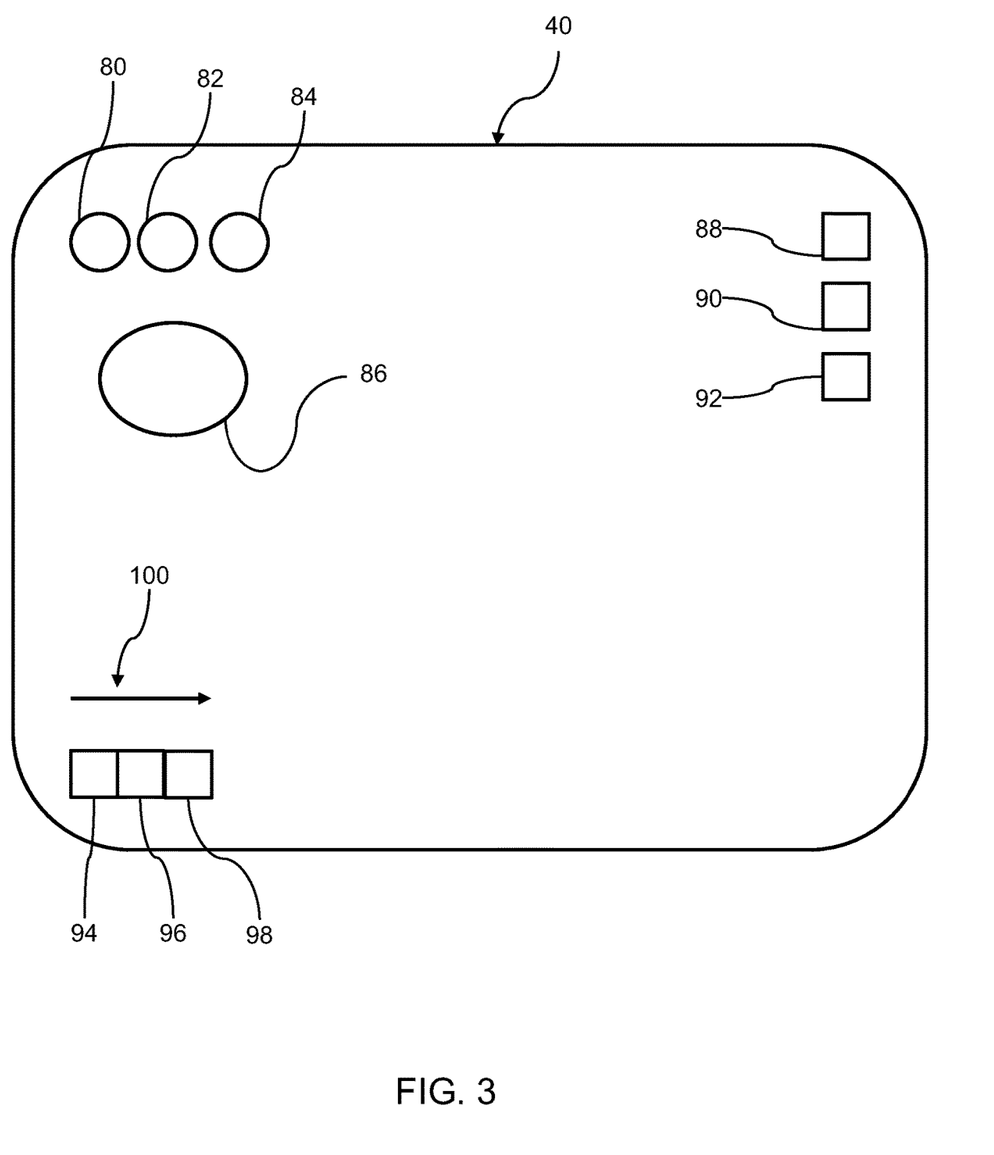
FIG. 3 shows a screen display of the system of FIG. 1 or FIG. 2.

An example of the display is shown in FIG. 3. In this example, the display is the same unit as the display 40 of FIG. 1 which shows the ultrasound images. However, as indicated above, it could be a dedicated display 74. In either case, it should be visible to the user during the process of acquiring the images, to enable the user to react to it and make appropriate adjustments.

In the example of FIG. 3, one small lamp 80, 82, 84 (i.e. in each case a color displayed at a predetermined area of the screen) for each of three different constraints indicates, using e.g. the traffic light color coding, the level of compliance at the moment. A bigger lamp 86 indicates by its color a score for the best joint compliance of the images in relation to the respective single constraints across the history of the current recording. In addition, colored squares 88, 90, 92, in a sequence matching that of the lamps 80, 82 and 84, on the right of the screen indicate, for each individual past recording, how consistent it is on average with the best match from the live acquisition. Colored squares 94, 96 and 98 on the bottom left indicate the consistency of the images between the most recently completed and the N previous cardiac cycles of the current live acquisition, in a time sequence from left to right, shown by the time arrow 100; in this example N=2.

Thus in the screen of FIG. 3 a cumulative indicator can be provided, which denotes how well the set of constraints has been fulfilled during the last cardiac cycle. Once the user starts a recording, i.e. enters the recording from the live view mode, the indicator can also be used to indicate how well the set was met in any best cardiac cycle since the recording has been started. This provides feedback on whether the recording has already sufficiently captured the desired kind of data or whether further cardiac cycles would be beneficial.

As mentioned earlier, indicators 94, 96 and 98 indicate the consistency of the last full cardiac cycle with a certain history of past cycles. This consistency may arise from the extent to which the overall set of constraints is met or from the agreement of user-defined measured quantities. This could check reproducibility of the acquisition. Finally, while a recording is done, its consistency with respect to a set of recent, stored recordings can be indicated. Consistency can be computed and expressed as described earlier.

The visual indications can of course be provided in any convenient and practical way, and need not be part of a screen display. They could be LED displays on the desktop equipment.

The compliance with the constraints can be expressed on a discrete scale (e.g. fulfilled, almost fulfilled, moderately fulfilled, or unmet). The traffic light sequence is an example, where green would be fulfilled, amber would be almost or moderately fulfilled, and red would be unmet. The extent to which a spatial FOV constraint is met, for example, can be described based on how much and how far the segmented delineation exceeds the limits of the current field of view. This level of compliance can be indicated in any of a variety of ways in the screen display of FIG. 3.

Figure 4:
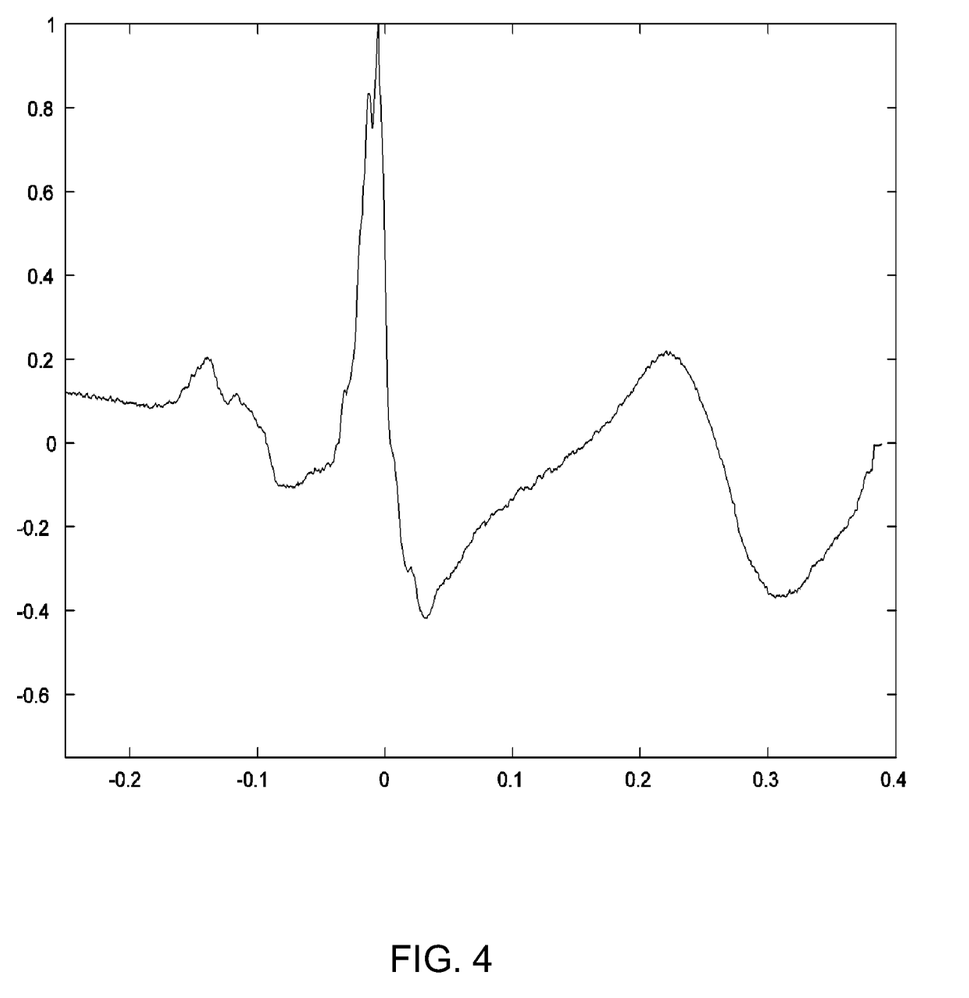
FIG. 4 shows a typical ECG trace.

The compliance monitoring unit 66 processes the image data and links it to additional information such as an ECG signal, which denotes the heartbeat phase, in the cardiac cycle, for the acquisition. An example of a typical ECG signal is shown in FIG. 4, in which a normalized signal is plotted against time in seconds along the horizontal axis. The processing involves a quick model-based segmentation of the image in the segmentation processor 56 to enrich the input ultrasound data with anatomical information (e.g. location of the chambers, valves or surrounding vessels). To quicken the segmentation process, the segmentation of one frame can be initialized with the segmentation from the previous frame to minimize the extent of adaptation that is required. After the model-based segmentation, the anatomical sites can be linked to the image data as well as to the cardiac phase via ECG. In a more basic version of the system without ECG, the cardiac phase can be estimated directly from the model-based segmentation.

Figure 5:
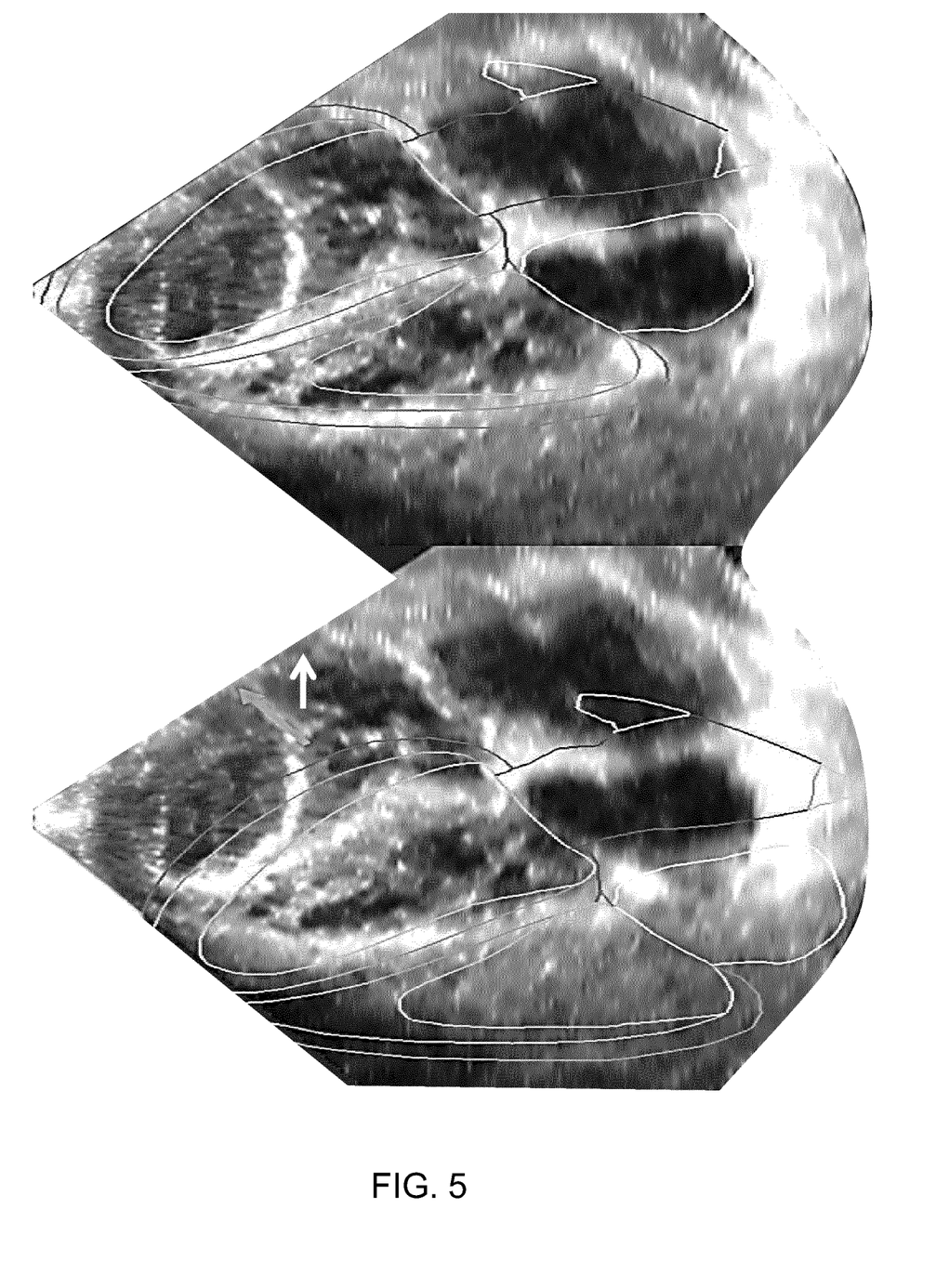
FIG. 5 is an image of a heart model mapped onto another cardiac ultrasound image.

An example of model-based segmentation of the heart is shown figuratively in FIG. 5, in which the loops superimposed on the 2D slice image are geometric shapes in a model of recognized regions of the heart anatomy. The spatial location is shown as being translated between the two images during an automatic correction process, starting with the bottom image and ending with the top image.

Using this information, the compliance with an activated set of constraints can be checked. This set of constraints is either manually provided by the user or read from the database 64 that stores guidelines for optimal acquisition in case of specific clinical applications. The compliance monitoring unit 66 compares the ultrasound data and the anatomical segmentation data from the anatomical data extraction unit 54 with the current set of constraints in the constraints determination unit 62, to output the comparison result to the feedback unit 68. Constraints can, for instance, be implemented as a set of primitives that can be parameterized by the user. Temporal constraints, for example, could take the form of an interval within the cardiac cycle (maximum range from 0% to 100%). Spatial constraints can be landmarks that can be, but are not restricted to, primitives like IS_IN_FOV (field of view), where the user can pass a set of pre-defined anatomical sites that are required to lie within the field of view, or like IS_CLOSE, where the user can pass a set of landmarks such as the aortic leaflet tips, which should be close to each other. Image quality constraints may include the level of contrast within the image, i.e. the visibility of features of interest.

For TAVI, transcatheter aortic valve implantation, for example, device selection and sizing should be done from a 3 chamber view on the aorta (a spatial constraint) during early systole (a temporal constraint), where the widest diameter can be measured [Kasel, A. M.; Cassese, S.; Bleiziffer, S.; Amaki, M.; Hahn, R. T.; Kastrati, A. & Sengupta, P. P. Standardized imaging for aortic annular sizing: implications for transcatheter valve selection JACC Cardiovasc Imaging, 2013, 6, 249-262]. In another example, the measurement of the LV ejection fraction requires the left ventricle to fully lie within the imaged field of view and this requires a good image contrast at the endocardial border (a quality constraint).

In a more advanced version of the system, the compliance monitoring unit 66 not only monitors constraints which are required to provide a useful measurement conform to the image guidelines, but may also monitor the measurements (e.g. aortic valve diameter under the constraints) as such. This information can be used by the feedback unit 68 to evaluate not only consistency i.e. reproducibility of the images in terms of the degree to which the constraints are met, but also consistency with respect to the measurements. Consistency with respect to a measurement can of course be one of the constraints that are determined and applied.

The invention can be applied in any context where ultrasound imaging of the heart is required or recommended, such as diagnosis or treatment of cardiovascular disease. Particular importance is given for applications where dedicated acquisition guidelines have been published. The invention can guide acquisition and help to make sure that the acquired data is suitable for the desired measurements or evaluations. It can further aid reproducibility by checking across cardiac cycles or even across a set of stored recordings. As the invention is intended to support acquisition and to avoid poorly suited data or even re-acquisitions, it may usefully be used in ultrasound workstations such as the Philips EPIQ workstation.

As previously explained, the ultrasound image processing apparatus 2 may be configured to automatically map the heart model including LV, RV, LA and RA anatomical site models onto an ultrasound image, preferably a volumetric ultrasound image, comprising an image of the heart of the subject (patient), typically but not necessarily a cross-sectional view of the patient's heart, for example using the mapping algorithms disclosed in WO 2016/142204 A1. Such a heart model typically is a model-based segmentation algorithm utilizing prior knowledge with regard to the general structural layout of the heart, how the heart location varies within 3-D volumetric ultrasound images, how the heart shape varies between different patients and the ways in which the heart is imaged using ultrasound imaging.

Such mapping is typically followed by the automatic segmentation of the ultrasound image with the mapped heart model in order to automatically obtain measurements of the heart, e.g. measurement of parameters such as ejection fraction and cardiac output, which require the volume of blood in a heart chamber at various phases of the heart cycle to be delineated in two or three dimensional images of a heart chamber.

The user interface may be enhanced if the user control panel 38 includes a touchscreen or mouse or other such user input device. The user could for example use gestures such as wiping a screen, or clicking whilst positioning a pointer on the screen, applied in relation to the indicators described above, to display more detailed compliance or consistency information than is given only by the indicators. User interactivity with the feedback indicators could be provided through a mouse by clicking on the indicator(s) to request the more detailed feedback information to be displayed. For tablet-based ultrasound the display space would be quite limited, so the extra information need not be displayed until so requested. The information could then be displayed as a pop-up on the screen.

Upon it being established that the user acknowledges the mapping of the heart model on the cardiac ultrasound image displayed on the display 40, the cardiac ultrasound image is segmented by the segmentation processor 56 using any suitable segmentation algorithm as previously explained, after which the segmentation results are displayed on the display 74 or 40. Such segmentation results for example may include the measurement of dynamic cardiac parameters such as ejection fraction in order to enable the user to assess performance of the heart over a period of time, e.g. through one or more cardiac cycles.

It will be understood that the CMUT cells 8 may be operable in transmission mode only without receiving pulse echoes, for therapy.

Figure 2:
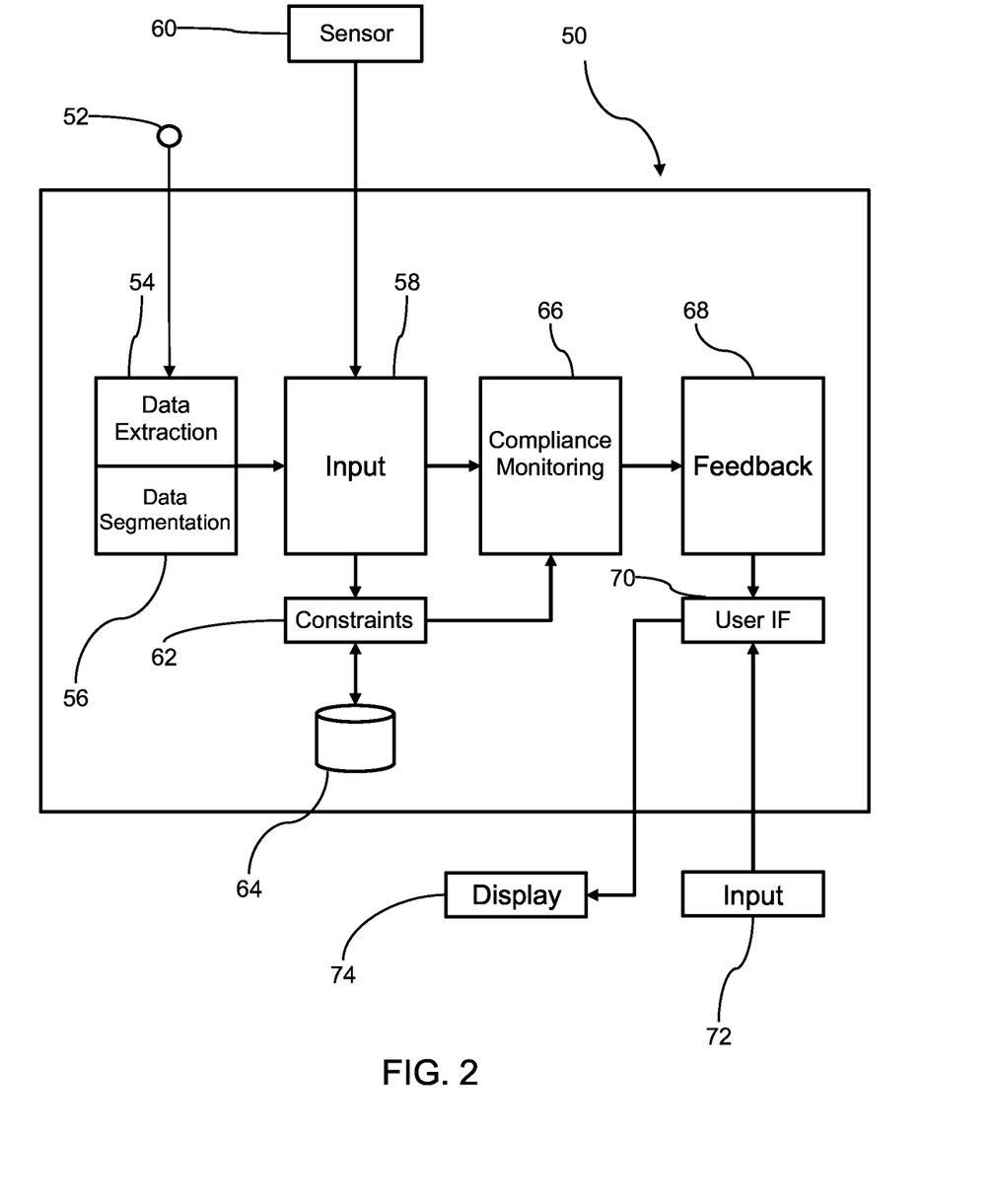
FIG. 2 shows part of the ultrasonic diagnostic imaging system of FIG. 1.
Figure 6:
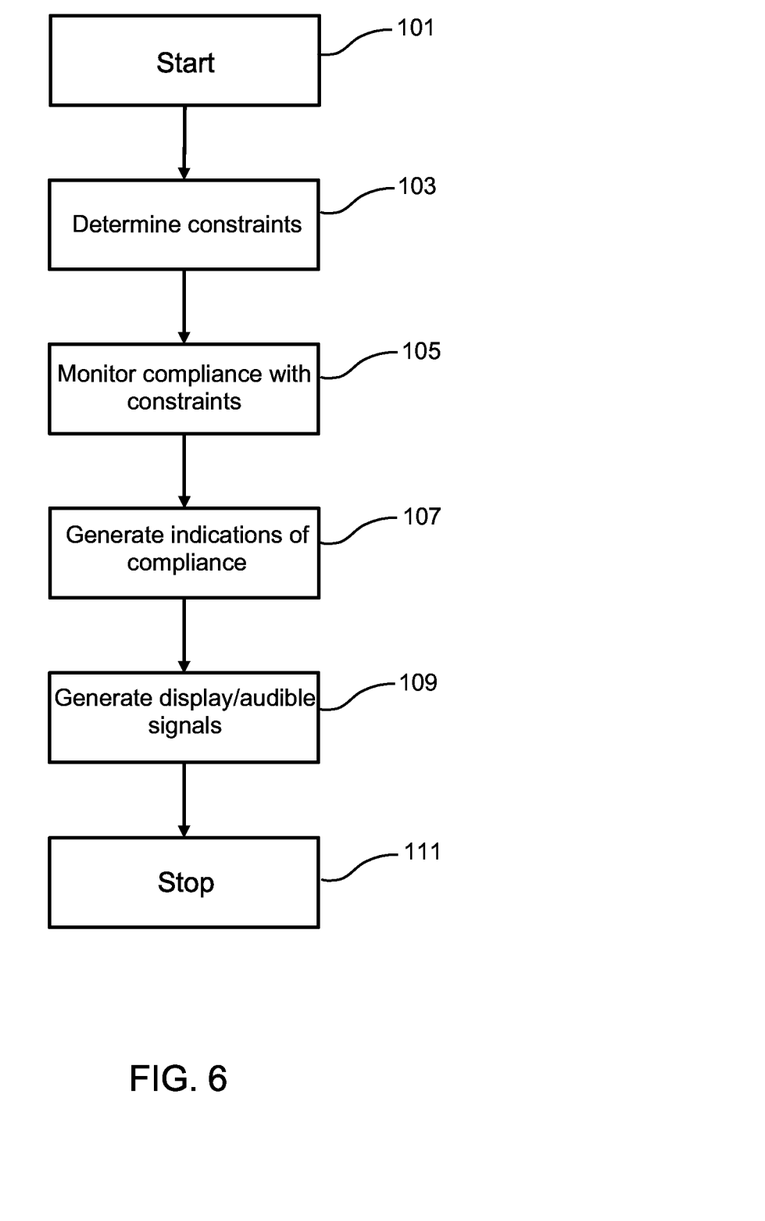
FIG. 6 shows a process carried out by the system of FIGS. 1 and 2.

FIG. 6 is a flow diagram of an example of a process using the system of FIGS. 1 and 2. In step 101 the ultrasound imaging process is started and the input unit 58 receives the ultrasound images and the segmentation results, preferably together with the physiological sensor data from the sensor 60. In step 103, the constraints determination unit 62 receives the data from the input unit 58 and compiles a set of current constraints, based on its interaction with the constraints database 64 to search for appropriate constraints and/or its receipt of constraints data from the user interface 70. In step 105 the compliance monitoring unit 66 monitors the input data for compliance with the current set of constraints, and provides an output to the feedback unit 68. In step 107 the feedback unit generates a set of indications based on the compliance, and provides this to the user interface 70. In step 109 the user interface generates signals for the display of the indications on the display 74, and any audible signals for its speaker. In step 111 the controller 50 responds to an input from the user using the input unit 72, communicating the user's decision to stop the ultrasound acquisition process based on favorable indications, to stop the process.

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions to be executed in whole or in part on the processor arrangement of the ultrasound image processing apparatus, such that the instructions create means for implementing the functions/acts specified in the flowchart and/or block diagram block or blocks. These computer program instructions may also be stored in a computer-readable medium that can direct the ultrasound image processing apparatus to function in a particular manner.

The computer program instructions may be loaded onto the processor arrangement to cause a series of operational steps to be performed on the processor arrangement, to produce a computer-implemented process such that the instructions which execute on the processor arrangement provide processes for implementing the functions/acts specified in the flowchart and/or block diagram block or blocks. The computer program product may form part of the ultrasound image processing apparatus 10, e.g. may be installed on the ultrasound image processing apparatus 10.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. Such a system, apparatus or device may be accessible over any suitable network connection; for instance, the system, apparatus or device may be accessible over a network for retrieval of the computer readable program code over the network. Such a network may for instance be the Internet, a mobile communications network or the like. More specific examples (a non-exhaustive list) of the computer readable storage medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of the present application, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out the methods of the present invention by execution on the processor arrangement may be written in any combination of one or more programming languages, including an object oriented programming language such as Java, Smalltalk, C++ or the like and conventional procedural programming languages, such as the "C" programming language or similar programming languages. The program code may execute entirely on the processor arrangement as a stand-alone software package, e.g. an app, or may be executed partly on the processor arrangement and partly on a remote server. In the latter scenario, the remote server may be connected to the ultrasound image processing apparatus 10 through any type of network, including a local area network (LAN) or a wide area network (WAN), or the connection may be made to an external computer, e.g. through the Internet using an Internet Service Provider.

As discussed above, embodiments make use of a controller. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An ultrasound imaging system for acquiring ultrasound images of an anatomical feature of interest in a subject, the system comprising:
   an input for receiving the ultrasound images;
   a controller operable by a user and configured to:
      store the ultrasound images;
      process the ultrasound images to extract anatomical data;
      determine constraints to be applied to the ultrasound images derived from the extracted anatomical data and/or on user input, wherein the constraints comprise a spatial constraint, a temporal constraint and an image quality constraint;
      monitor the ultrasound images, as the ultrasound images are received, for determining compliance of the ultrasound images with the determined constraints based on how well the constraints have been met by the ultrasound images; and
      generate indications based on the determined compliance of the ultrasound images with the determined spatial, temporal and image quality constraints, respectively, wherein each indication separately indicates a level of compliance with a corresponding one of the determined spatial, temporal and image quality constraints; and
   an output for providing the indications to the user.

2. The system according to claim 1, wherein the controller comprises a segmentation processor configured to segment the ultrasound images in accordance with a mapped model of the anatomical feature of interest, wherein the anatomical data is extracted from the segmented ultrasound images.

3. The system according to claim 1, further comprising a database of image constraints in relation to anatomical data, the controller being configured to obtain the constraints from the database.

4. The system according to claim 1, wherein the controller is configured to receive physiological data relating to the subject from at least one body sensor and to determine the compliance of the ultrasound images with the determined constraints based at least in part on the physiological data.

5. The system according to claim 1, wherein the controller is configured to store the determined compliance of the ultrasound images with the determined constraints over successive periods, to determine whether a predetermined image type has been received, and to provide an indication to the user based on whether the predetermined image type has been received.

6. The system according to claim 1, wherein the controller is configured to provide separate visual and/or aural indications to the user based on the determined compliance of the ultrasound images with the determined spatial, temporal and image quality constraints, respectively.

7. The system according to claim 1, further comprising:
a monitor arranged to display to the user the received ultrasound images and the output,
wherein the output comprises a light display configured to display the indications based on the determined compliance of the ultrasound images with the determined spatial, temporal and image quality constraints,
wherein each indication is configured to provide a plurality of different colors, wherein each color of the plurality of different colors corresponds to a different level of compliance with the corresponding one of the determined spatial, temporal and image quality constraints.

8. The system according to claim 1, wherein the ultrasound images are heart images of a heart of the subject and the controller is configured to monitor the heart images for compliance with the spatial constraint and with the temporal constraint in relation to a heartbeat cycle.

9. The system according to claim 1, wherein the spatial constraint is on a field of view or a location or angle of imaging the anatomical feature of interest, and the temporal constraint is on a period of imaging the anatomical feature of interest.

10. A computer-implemented ultrasound imaging method of acquiring ultrasound images of an anatomical feature of interest in a subject, the ultrasound imaging method comprising:
receiving the ultrasound images;
storing the ultrasound images;
processing the ultrasound images to extract anatomical data of the anatomical feature of interest;
determining constraints to be applied to the ultrasound images based on the extracted anatomical data and/or on user input by a user, wherein the constraints comprises a spatial constraint, a temporal constraint and an image quality constraint;
monitoring the ultrasound images, as the ultrasound images are received, for determining compliance of the ultrasound images with the determined constraints based on how well the constraints have been met by the ultrasound images;
providing indications based on the determined compliance of the ultrasound images with the determined spatial, temporal and image quality constraints, respectively, wherein each indication separately indicates a level of compliance with a corresponding one of the determined spatial, temporal and image quality constraints;
providing the indications to the user.

11. The ultrasound imaging method according to claim 10, wherein processing the ultrasound images comprises segmenting the ultrasound images in accordance with a mapped model of the anatomical feature of interest.

12. The ultrasound imaging method according to claim 10, further comprising:
receiving the ultrasound images until a predetermined image type has been received;
providing an indication to the user that predetermined image type has been received; and
continuing the processing of the ultrasound images on received ultrasound images of a different image type.

13. A non-transitory computer readable storage medium storing computer readable program instructions that, when executed by a processor, cause the processor to implement:
receive ultrasound images of an anatomical feature of interest of a subject;
store the ultrasound images;
process the ultrasound images to extract anatomical data;
determine constraints to be applied to the ultrasound images based on the extracted anatomical data and/or on user input, wherein the constraints comprise a spatial constraint, a temporal constraint and an image quality constraint;
monitor the ultrasound images, as the ultrasound images are received, for determining compliance of the ultrasound images with the determined constraints based on how well the constraints have been met by the ultrasound images;
provide indications based on the determined compliance of the ultrasound images with the determined spatial, temporal and image quality constraints, respectively, wherein each indication separately indicates a level of compliance with a corresponding one of the determined spatial, temporal and image quality constraints;
provide the indications to a user in real time.

14. The ultrasound imaging method of claim 10, further comprising:
obtaining the constraints from a database.

15. The ultrasound imaging method of claim 10, further comprising:
receiving physiological data relating to the subject from at least one body sensor, wherein the compliance of the ultrasound images with the determined constraints is determined based at least in part on the physiological data.

16. The ultrasound imaging method of claim 10, further comprising:
storing the determined compliance of the ultrasound images over successive periods;
determining whether a predetermined image type has been received; and
providing an indication to the user based on whether the predetermined image type has been received.

17. The ultrasound imaging method of claim 10, further comprising:
providing separate visual and/or aural indications to the user based on the determined compliance of the ultrasound images with different respective constraints of the determined constraints.

18. The system according to claim 7, wherein the plurality of different colors comprise a first color indicating the level of compliance as fulfilled, a second color indicating the level of compliance as moderately fulfilled, and a third color indicating the level of compliance as unmet for each of the determined spatial, temporal and image quality constraints.

19. The system according to claim 1, wherein the controller is further configured to:
- store the ultrasound images and to compare currently received ultrasound images with the stored ultrasound images to determine consistency of corresponding degrees of compliance with the spatial, temporal and image quality constraints, respectively; and
- generate additional indications based on the determined consistency of corresponding degrees of compliance of the ultrasound images with the determined spatial, temporal and image quality constraints, respectively, wherein each additional indication indicates a level of consistency for a corresponding one of the determined spatial, temporal and image quality constraints.

20. The ultrasound imaging method of claim 10, further comprising:
- storing the ultrasound images and comparing currently received ultrasound images with the stored ultrasound images to determine consistency of corresponding degrees of compliance with the spatial, temporal and image quality constraints, respectively; and
- generating additional indications based on the determined consistency of corresponding degrees of compliance of the ultrasound images with the determined spatial, temporal and image quality constraints, respectively, wherein each additional indication indicates a level of consistency for a corresponding one of the determined spatial, temporal and image quality constraints.

* * * * *